United States Patent [19]

Hirsh

[11] Patent Number: 4,587,215
[45] Date of Patent: May 6, 1986

[54] HIGHLY THERMOSTABLE AMYLOGLUCOSIDASE

[75] Inventor: Jody K. Hirsh, Glenview, Ill.

[73] Assignee: UOP Inc., Des Plaines, Ill.

[21] Appl. No.: 624,448

[22] Filed: Jun. 25, 1984

[51] Int. Cl.$^4$ .......................... C12P 19/20; C12N 9/34; C12R 1/645
[52] U.S. Cl. ...................................... 435/96; 435/205; 435/911
[58] Field of Search ................................ 435/96, 205

[56] References Cited

U.S. PATENT DOCUMENTS 4,247,637  1/1981  Tamura et al. ........................ 435/96

OTHER PUBLICATIONS

American Type Culture Collection Catalogue of Strains I, 15th Edition, 1982, p. 512.

Primary Examiner—Lionel M. Shapiro
Attorney, Agent, or Firm—Thomas K. McBride; William H. Page, II; Eugene I. Snyder

[57] ABSTRACT

Microorganisms of the species *Talaromyces thermophilus* elaborate an amyloglucosidase which shows remarkable thermostability. The enzyme shows biphasic decay, where an initial decay, corresponding to loss of 25–40% activity, is followed by essentially no further loss in activity at 70° C. under conditions where a prior art thermostable amyloglucosidase showed a half-life of 53 minutes.

7 Claims, 1 Drawing Figure

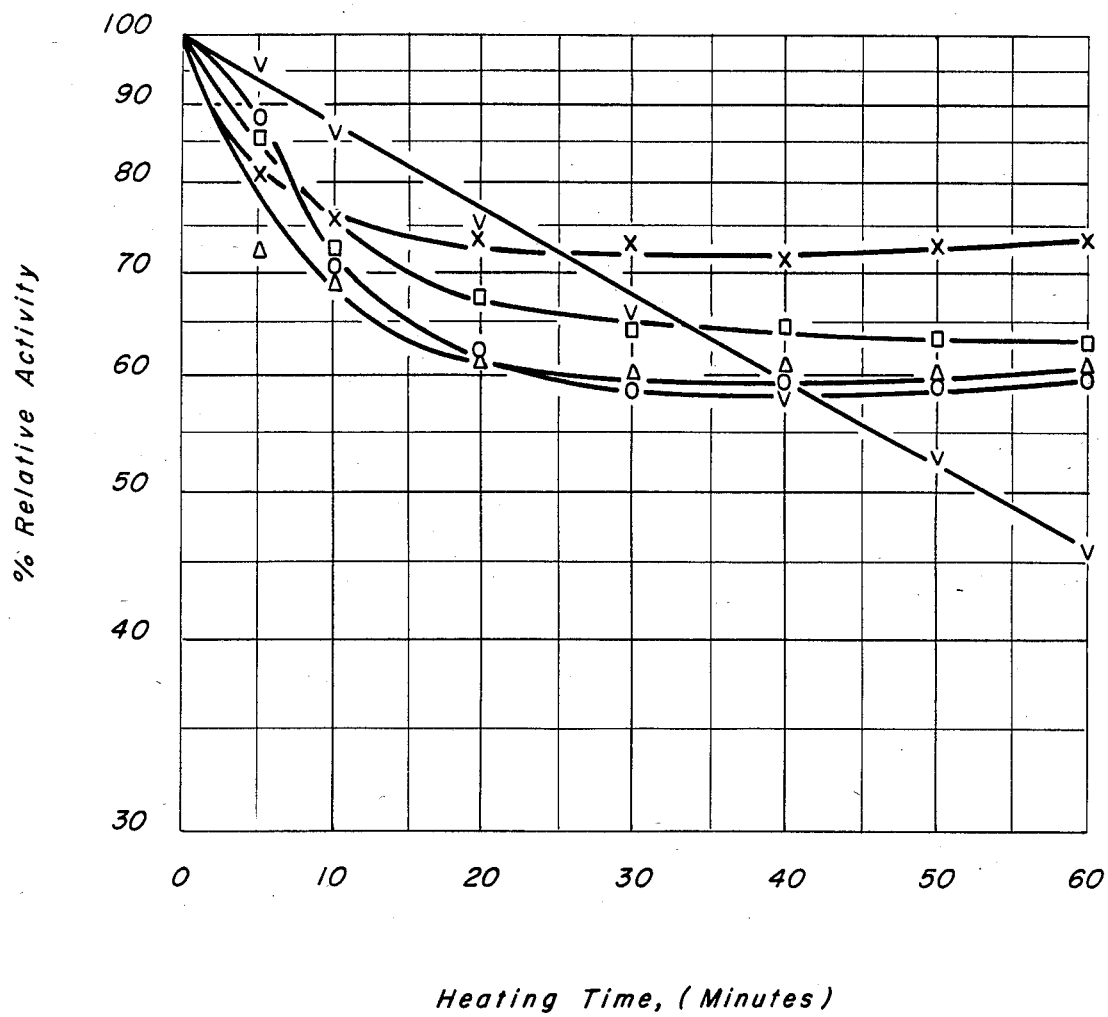

HIGHLY THERMOSTABLE AMYLOGLUCOSIDASE

BACKGROUND OF THE INVENTION

The conversion of starch to glucose generally is effected in two discrete processes. Initially the starch is partially hydrolyzed, either by acid or by enzymes. The partially hydrolyzed starch (starch hydrolysate, thinned starch) typically contains only a few percent glucose and is the substrate for amyloglucosidase (glucoamylase), hereafter denoted AG, an enzyme which completes the hydrolysis of polysaccharides to glucose.

The most commonly utilized source of AG is microorganisms from the genus Aspergillus, and the AG catalyzed hydrolysis of thinned starch is most commonly performed batchwise. When considering continuous methods of hydrolyzing thinned starch, especially those where the enzyme is to be reused, it soon becomes apparent that thermostability of AG is an important factor for several reasons. One reason is that the higher its thermostability, the longer will be the enzyme lifetime, hence the greater will be its effective utilization. Another factor is the higher productivity per unit time resulting from higher temperatures. Yet another factor is that microbial contamination is reduced at higher temperature.

U.S. Pat. No. 4,247,637 describes a thermostable AG elaborated by a microorganism isolated from the soil and identified as *Talaromyces duponti*. This application describes an AG remarkably more thermostable than that disclosed above.

SUMMARY OF THE INVENTION

One aspect of this invention is a method of making a thermostable AG by culturing microorganisms of the species *Talaromyces thermophilus* in a nutrient medium. In another aspect the invention herein is a thermostable AG elaborated by microorganisms of the species *Talaromyces thermophilus*. In yet another aspect the invention is a method of making glucose by enzymatic hydrolysis of thinned starch using the thermostable AG of this invention.

DESCRIPTION OF THE FIGURE

FIG. 1 shows the thermal decay of the AG produced by several varieties of microorganisms from the species *Talaromyces thermophilus* compared with that from *Talaromyces duponti*.

DESCRIPTION OF THE INVENTION

Although many microorganisms elaborate an amyloglucosidase as part of their arsenal of enzymes, I have discovered that the AG produced by microorganisms of the species *Talaromyces thermophilus* are remarkably thermostable, as is shown in FIG. 1. These AGs all show biphasic decay, that is, their loss of activity occurs in two distinct phases with the initial period of rapid decay followed by a period of very slow decay at 70° C. At that temperature and pH 5.0 in the absence of substrate the half-life for the fast decay is about 18 minutes, with no measurable loss of activity within an hour in the second phase of decay. In contrast, *Talaromyces duponti* shows a linear decay with a half-life of about 53 minutes under the same conditions.

The AGs of this invention retain from about 60% to about 75% of their activity after the initial phase of decay; it is to be emphasized that further loss of activity under the aforementioned conditions occurs very slowly.

EXAMPLE 1 MICROORGANISM GROWTH AND ENZYME STABILITY

Lyophilized samples of varieties of *Talaromyces thermophilus* obtained from the American Type Culture Collection were streaked out and grown on an agar plate. A sample from the plate was inoculated on a culture slant of yeast extract starch agar at 45° C. for two weeks until the microorganisms were well sporulated. The slant medium was: Difco yeast extract, 0.4%, soluble starch, 1.5%; $K_2HPO_4$, 0.1%; $MgSO_4$, 0.05%; agar, 2.0%. An inoculum from the slant then was grown in a medium consisting of 5% soluble starch, 2% corn steep liquor, 1.0% cottonseed meal, 0.5% yeast extract, 0.1% $K_2HPO_4$, 0.05% $MgSO_4$, and 0.01% $CaCl_2$ adjusted to pH 7.0. Growth was continued for two weeks at 40° C. on an orbital shaker at 200 rpm, cultures were harvested by filtration, and the filtrates were used as the source of crude AG. The same procedure was used to grow *Talaromyces duponti*, strain G45-632, as obtained from the Fermentation Research Institute of Japan, Deposit No. 4566. The AG activity in the filtrate is summarized in the following table.

| Microorganism | | AG activity, IU/ml |
|---|---|---|
| *Talaromyces thermophilus*, | NRRL 15774 | 8.4 |
| | NRRL 15775 | 7.0 |
| | NRRL 15776 | 6.4 |
| | NRRL 15777 | 6.6 |
| *Talaromyces duponti*, | G45-632 | 5.6 |

It can be seen that all of the listed strains produced about the same amount of AG. The filtrate AG activity from *Talaromyces duponti* was found to be substantially lower than the 60 units per ml claimed in the prior art. Significantly, no AG was produced by *Talaromyces duponti* in the absence of cottonseed meal in the medium, whereas the two thermophilus species so tested (NRRL 15774 and 15777) did elaborate AG.

The thermostability of the AGs were determined as follows. A 5 ml sample of each filtrate, adjusted to a pH of 5.0, was heated at 70° C. for 60 minutes, with 0.5 ml samples removed periodically and immediately placed and retained in an iced water bath. After all samples were taken they were permitted to warm to room temperature and 0.2 ml portions were assayed. The results are shown in FIG. 1. All strains of *Talaromyces thermophilus* displayed biphasic decay, with the half-life of the first phase decay of AG from NRRL 15777 being about 18 minutes. None of the thermophilus strains showed any appreciable decay beyond that in the first phase. In contrast, the AG from *Talaromyces duponti* showed a first order decay with a half-life of about 53 minutes.

That the AG from microorganisms of the species *Talaromyces thermophilus* is distinct from that of *Talaromyces duponti* is indicated by the differing thermal behavior of the two classes of enzymes and is confirmed by other physical measurements such as electrophoretic mobility and molecular weight determination.

EXAMPLE 2 DISC-POLYACRYLAMIDE GEL ELECTROPHORESIS

The procedure followed was that of D. E. Williams and R. A. Reisfeld, *N.Y. Academy of Science*, 121, 373-81 (1964) with a pH 6.8 stacking gel and a pH 8.3 separating gel. A slab gel was used with duplicate samples run. Approximately 5 micrograms protein per lane was used for total protein staining with Coomassie Blue (one-half of gel) and approximately 10 micrograms protein per lane for the activity stain (other half of gel). Following electrophoresis the gel was cut in half, with one-half stained for protein and the other half stained for AG activity.

The activity stain was specific for the detection of glucose production from starch hydrolysis by formation of a red color. The reagents were 4.0% soluble starch containing 0.1 molar sodium acetate at pH 4.5 (A), 1% 4-aminoantipyrine in 20% aqueous ethanol and 0.04 molar phenol (B), amylase-free glucose oxidase, 1,000 units per ml (C), horseradish peroxidase, 265 units per ml (D), and 2% melted agar at 40° C. (E). Three parts A, one part B, 0.2 parts C, 0.1 part D, and two parts E were quickly mixed and used to overlay the gel. This is incubated at 60° C. for 10–20 minutes. Formation of a red color indicates glucose production, and in this way the AG-active protein in the various bands formed on electrophoresis could be unequivocally identified.

Samples were run of the concentrated crude filtrate described in Example 1. Additionally, an AG concentrate obtained from the assignee of U.S. Pat. No. 4,247,637 was used. All thermophilus strain protein patterns were similar to each other and distinct from the protein patterns from G45-632 and the AG concentrate from the aforementioned assignee, with the latter two being identical for the AG active protein. All thermophilus strains showed a relative mobility, $R_f$, for the Ag active protein of 0.63, whereas that from strain G45-632 and the assignee's AG concentrate was 0.5.

EXAMPLE 3 MOLECULAR WEIGHT DETERMINATION

Molecular weight was determined by gel permeation high pressure liquid chromatography using in series columns of Altex Spherogel TSK G2000 and 3000 SW, each 30 centimeters long by 8 mm id. The solvent was 0.2 molar $K_2HPO_4$ at pH 6.8 at a flow rate of 0.5 ml per minute. A UV detector at 280 nanometers was used 0.2 absorbance units full scale. Calibration standards included thyroglobulin (670,000), gamma-globulin (158,000 ), bovine serum albumin (66,000), ovalbumin (44,000), myoglobin (17,000), and vitamin $B_{12}$ (1350).

A crude filtrate from *Talaromyces thermophilus*, NRRL 15777, concentrated via alcoholic precipitation, was used as one enzyme source. The other sample tested was the AG concentrate from the aforementioned assignee. Enzyme samples were injected in duplicate. Samples from the various peaks on ellution were collected and assayed for AG activity to unequivocally identify the AG active material. From the chromatogram and using the standards described above it was determined that the AG from *Talaromyces duponti* had a molecular weight of about 133,000, whereas that from *Talaromyces thermophilus*, NRRL 15777, had a molecular weight of about 45,000.

To complete the distinction, the AGs of this invention show a maximum enzyme activity of about 1 pH unit higher than that from *Talaromyces duponti*.

EXAMPLE 4 ACTIVITY-pH PROFILE

The aforementioned Ag concentrate from *Talaromyces duponti* was diluted 1:1000 in distilled water. The AG from NRRL 15777, grown in a medium of 2% starch, 2% corn steep liquor, 0.5% Amber BYF yeast extract, with minerals and the pH the same as that of Example 1, was a crude culture filtrate. A citrate-phosphate buffer system was used for the pH range 2.6–7.6 and used in equal volumes with the AG sample. The actual pH of each sample so prepared was measured and the AG activity at 60° C. was assayed. Results are summarized in the following table, which shows the activity maximum of the thermophilus AG is about one pH unit higher than the duponti AG.

| AG from *Talaromyces duponti* | | AG from *Talaromyces thermophilus*, NRRL 15777 | |
|---|---|---|---|
| pH | % relative activity | pH | % relative activity |
| 2.4 | 80 | 3.52 | 28 |
| 2.84 | 86 | 4.00 | 82 |
| 3.18 | 94 | 4.41 | 90 |
| 3.71 | 96 | 5.05 | 100 |
| 4.16 | 100 | 5.41 | 97 |
| 4.74 | 94 | 5.90 | 91 |
| 5.08 | 85 | 6.04 | 89 |
| 6.13 | 58 | 6.54 | 75 |
| 7.05 | 24 | 7.11 | 54 |
| 8.70 | 0 | 8.13 | 26 |

The amyloglucosidases of this invention are used to complete the hydrolysis of partially hydrolyzed starch to glucose, a process generally referred to as saccharification. Saccharification may be conducted either batchwise or continuously using either the free enzyme or an immobilized AG. Saccharification using the AGs of this invention is preferably done in a continuous process using either free or immobilized AG. It is preferred that the temperature at which saccharification is performed be relatively high to utilize the advantages of the thermostable AGs of this invention. In practice this means performing the hydrolysis at a temperature between about 55° C. and about 100° C., desirably between about 60° C. and 90° C. Saccharification may be effected at a pH between about 4.0 and about 6.5.

In all cases the enzyme activity assay was performed as follows. A sample (0.5 ml) of material whose enzymatic activity was to be assayed was mixed with 0.5 ml of a 2.0% solution of thinned starch (Maltrin M-100) in a sodium acetate buffer, pH 4.5, 0.1 molar, and maintained at 60° C. for 10–30 minutes. The reaction was quenched by the addition of 0.5 ml 0.5N NaOH. A blank was prepared by adding to 0.5 ml of the NaOH solution a 0.5 ml sample of enzyme preparation and 0.5 ml of the buffered thinned starch solution, without incubation at 60° C. Glucose is then measured by any suitable method, e.g., a glucose analyzer. The resulting AG activity, expressed in International units per ml (Iu/ml) is calculated according to the equation $$\frac{(S - B) \times V_t}{t \times V_E \times 0.18}$$

where
S = Glucose concentration of sample in mg per ml,
B = glucose concentration of blank in mg per ml,
$V_t$ = total volume of assay mixture after quenching in ml,
t = incubation time in minutes,
$V_E$ = volume of enzyme assayed in ml
0.18 = molecular weight of glucose, expressed in mg per μmole.

What is claimed is:

1. A method of making a thermostable amyloglucosidase exhibiting biphasic decay at 70° C. and pH 5 in the absence of substrate with a half-life of first phase decay of about 18 minutes and no measurable second phase decay for the next hour, with retention of at least about 60% of its original activity after the first phase decay, with an electrophoretic relative mobility of about 0.63 using a polyacrylamide gel at pH 8.3, and having maximum enzymatic activity at about pH 5.1 with 90% of its maximum activity in the pH range from about 4.4 to about 6.0, comprising culturing a microorganism from the species *Talaromyces thermophilus* in a nutrient medium and recovering the amyloglucosidase produced thereby.

2. The method of claim 1 where the microorganism is NRRL 15774, 15775, 15776, or 15777.

3. The method of claim 2 where the microorganism is NRRL 15777.

4. A method of making glucose comprising contacting at saccharification conditions a feedstock of partially hydrolyzed starch with the thermostable amyloglucosidase of claim 1.

5. A thermostable amyloglucosidase elaborated by microorganisms of the species *Talaromyces thermophilus* when grown in a nutrient medium, said amyloglucosidase exhibiting a biphasic decay at 70° C. and pH 5 in the absence of substrate with a half-life of first phase decay of about 18 minutes and no measurable second phase decay for the next hour, with retention of at least about 60% of its original activity after the first phase decay, with an electrophoretic relative mobility of about 0.63 using a polyacrylamide gel at pH 8.3, and having maximum enzymatic activity at about pH 5.1 and 90% of its maximum activity in the pH range from about 4.4 to about 6.0.

6. The thermostable amyloglucosidase of claim 5 where the microorganism is NRRL 15774, 15775, 15776, or 15777.

7. The thermostable amyloglucosidase of claim 6 where the microorganism is NRRL 15777.

* * * * *